US006261578B1

(12) United States Patent
Dupuis

(10) Patent No.: US 6,261,578 B1
(45) Date of Patent: Jul. 17, 2001

(54) COSMETIC COMPOSITION CONTAINING A POLYSACCHARIDE AND AN ACRYLIC TERPOLYMER, AND USE OF THIS COMPOSITION FOR THE TREATMENT OF KERATINOUS MATERIAL

(75) Inventor: Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/332,006

(22) Filed: Jun. 14, 1999

(30) Foreign Application Priority Data

Jun. 15, 1998 (FR) .................................................. 98 07515

(51) Int. Cl.[7] .............................. A61K 7/00; A61K 7/42; A61K 7/06; A61K 7/11
(52) U.S. Cl. ........................... 424/401; 424/59; 424/70.1; 424/70.11; 424/70.13; 424/70.16; 424/70.9
(58) Field of Search .................... 424/401, 70.1, 424/70.11, 70.13, 70.16, 59, 70.9

(56) References Cited

U.S. PATENT DOCUMENTS

| 4,472,297 | * | 9/1984 | Bolich, Jr. et al. | 252/531 |
|---|---|---|---|---|
| 4,514,552 | * | 4/1985 | Shay et al. | 526/301 |
| 5,015,711 | | 5/1991 | Simonet et al. | 526/301 |
| 5,066,710 | | 11/1991 | Simonet et al. | 524/555 |
| 5,277,899 | * | 1/1994 | McCall | 424/71 |
| 5,294,693 | | 3/1994 | Egraz et al. | 526/310 |
| 5,362,415 | | 11/1994 | Egraz et al. | 252/174.24 |
| 5,405,900 | * | 4/1995 | Jenkins et al. | 524/556 |
| 5,977,036 | * | 11/1999 | Guskey | 510/121 |

FOREIGN PATENT DOCUMENTS

| 0173109 | 3/1986 | (EP) . |
|---|---|---|
| 0350414 | 1/1990 | (EP) . |
| 0577526 | 1/1994 | (EP) . |
| 0 824 914 | 2/1998 | (EP) . |
| WO93/24544 | 12/1993 | (WO) . |

* cited by examiner

*Primary Examiner*—Shelley A. Dodson
*Assistant Examiner*—Marina Lamm
(74) *Attorney, Agent, or Firm*—Jacobson, Price, Holman & Stern, PLLC

(57) ABSTRACT

The present application relates to cosmetic compositions containing, in a cosmetically acceptable aqueous medium, at least one polysaccharide and an acrylic terpolymer, as well as to the use of these compositions for treating the skin or the hair.

The acrylic terpolymer comprises:

a) about 20 to 70% by weight of a carboxylic acid containing α, β-monoethylenic unsaturation;

b) about 20 to 80% by weight of a non-surfactant monomer containing monoethylenic unsaturation, which is different from a), and c) about 0.5 to 60% by weight of a nonionic urethane monomer which is the product of reaction of a monohydric nonionic surfactant with a monoisocyanate containing monoethylenic unsaturation.

The polysaccharide is preferably a guar gum.

30 Claims, No Drawings

COSMETIC COMPOSITION CONTAINING A POLYSACCHARIDE AND AN ACRYLIC TERPOLYMER, AND USE OF THIS COMPOSITION FOR THE TREATMENT OF KERATINOUS MATERIAL

The present invention relates to cosmetic compositions containing, in combination, at least one polysaccharide and an acrylic terpolymer, as well as to the use of these compositions for the treatment of keratinous material, in particular the skin and the hair.

The polymers of polysaccharide type give a very good styling effect on the hair. However, most are not thickeners or, if they are, they give gels of insufficient viscosity or of runny texture.

It is then necessary, when it is desired to present them in the form of a styling gel or a care gel, to combine them with a thickener which gives them an adequate texture while at the same time retaining the good cosmetic performance of these products.

The thickeners most commonly used are generally based on crosslinked acrylic polymers, such as the products sold under the name "Carbopol" by the company Goodrich and those sold under the name "Synthalen K" by the company 3V. When used in combination with polysaccharides, these polymers usually lead to gels of unsatisfactory texture which are also unsatisfactory in terms of the cosmetic results since they do not give the hair good disentangling or softness properties; they do not have good fixing power either. Other thickening and/or gelling polymers are known which contain in their chain a hydrophilic part and a hydrophobic part consisting of a fatty chain, such as the product "Pemulen TR1" sold by the company Goodrich or the "Acrysol" polymers sold by the company Rohm & Haas. The polymer "Pemulen TR1", used in combination with polysaccharides, does not lead to a gel of satisfactory texture and does not give satisfactory cosmetic results, in particular as regards the fixing power. The polymer "Acrysol 44", in combination with a polysaccharide, leads to a very fluid and cloudy product.

The Applicant has discovered, surprisingly, that by using a novel family of thickening and/or gelling polymers and by combining them with polysaccharides, it is possible to obtain cosmetic formulations which have a satisfactory viscosity at a relatively low pH, which are not pasty, which spread well on the skin and hair and which give the hair good properties of softness and easy disentangling while at the same time having good fixing properties.

The subject of the present invention is thus cosmetic compositions containing, in a cosmetically acceptable aqueous support, at least one polysaccharide and an acrylic terpolymer which will be defined in greater detail later in the description.

This polymer makes it possible in particular to prepare leave-in or rinse-out, aqueous-organic or aqueous compositions containing cosmetically acceptable solvents, ranging from lightly gelled products to sticks or solid tubes.

The advantages of this terpolymer are that it is stable in electrolytic medium and has very good thickening power at a pH equal to or above 5.5, making it possible to achieve a good level of viscosity and to be able to use high concentrations of alcohol.

When used in combination with at least one polysaccharide, this polymer makes it possible to prepare gelled, non-pasty products which are easy to spread, soft to apply and have good fixing power. I This polymer also makes it possible to improve the conditioning effect of the polysaccharides on the hair, in particular its feel.

The acrylic terpolymer used in accordance with the invention is soluble or swellable in alkalis. It is characterized in that it comprises:

a) about 20 to 70% by weight, preferably 25 to 55% by weight, of a carboxylic acid containing a, β-monoethylenic unsaturation;

b) about 20 to 80% by weight, preferably 30 to 65% by weight, of a non-surfactant monomer containing monoethylenic unsaturation, which is different from a), and c) about 0.5 to 60% by weight, preferably 10 to 50% by weight, of a nonionic urethane monomer which is the product of reaction of a monohydric nonionic surfactant with a monoisocyanate containing monoethylenic unsaturation.

The carboxylic acid containing α, β-monoethylenic unsaturation a) can be chosen from many acids and in particular acrylic acid, methacrylic acid, itaconic acid and maleic acid. Methacrylic acid is preferred. A large proportion of acid is essential in order to give a polymer structure which dissolves and gives a thickening effect by reaction with an alkaline compound such as sodium hydroxide, alkanolamines, aminomethylpropanol or aminomethylpropanediol.

The terpolymer should also contain a large proportion, indicated above, of a monomer b) containing monoethylenic unsaturation which has no surfactant properties. The preferred monomers are those which give polymers that are water-insoluble when they are homopolymerized and are illustrated by $C_1$–$C_4$ alkyl acrylates and methacrylates such as methyl acrylate, ethyl acrylate and butyl acrylate, or corresponding methacrylates. The monomers more particularly preferred are methyl and ethyl acrylates. Other monomers which can be used are styrene, vinyltoluene, vinyl acetate, acrylonitrile and vinylidene chloride. Non-reactive monomers are preferred, such monomers being those in which the single ethylenic group is the only group which is reactive under the polymerization conditions. However, monomers which contain groups that are reactive under the action of heat can be used in certain situations, such as hydroxyethyl acrylate.

The monohydric nonionic surfactants used to obtain the nonionic urethane monomer c) are well known and are generally alkoxylated hydrophobic compounds containing an alkylene oxide forming the hydrophilic part of the molecule. The hydrophobes generally consist of an aliphatic alcohol or an alkylphenol in which a carbon chain containing at least six carbon atoms constitutes the hydrophobic part of the surfactant.

The preferred monohydric nonionic surfactants have the formula:

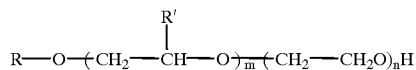

in which R is a $C_6$–$C_{30}$ alkyl or $C_8$–$C_{30}$ aralkyl group, R' is a $C_1$–$C_4$ alkyl group, n is an average number ranging approximately from 5 to 150 and m is an average number ranging approximately from 0 to 50, with the condition that n is at least as large as m and that n+m=5–150.

As preferred $C_6$–$C_{30}$ alkyl groups, mention may be made of dodecyl and $C_{18}$–$C_{26}$ alkyl radicals. As aralkyl groups, mention may be made more particularly of ($C_8$–$C_{13}$) alkylphenyl groups. The preferred group R' is the methyl group.

The monoisocyanate containing monoethylenic unsaturation which is used to form the nonionic urethane monomer c) can be chosen from a wide variety of compounds. A compound containing any copolymerizable unsaturation such as acrylic or methacrylic unsaturation can be used. An allylic unsaturation imparted by allyl alcohol can also be used. The preferred monoethylenic monoisocyanate is α,α-dimethyl-m-isopropenyl-benzylisocyanate.

The acrylic terpolymer defined above is obtained by aqueous emulsion copolymerization of the components a), b) and c) which is entirely common and described in patent application EP-A-0,173,109.

As terpolymers which can be used according to the invention, mention may be made of the products of reaction of methacrylic acid as component a), of ethyl acrylate as component b) and of a nonionic urethane macromonomer as component c), having the following structure:

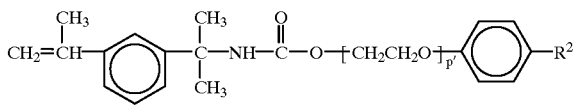

in which p' ranges from 6 to 150 and is preferably equal to 30 and $R^2$ is a $C_8$–$C_{13}$ alkyl radical, such as that described in Example 3 of patent application EP-A-0,173,109.

The preferred acrylic terpolymer used according to the invention is obtained from methacrylic acid as component a), methyl acrylate as component b) and a nonionic urethane macromonomer as component c), having the following structure:

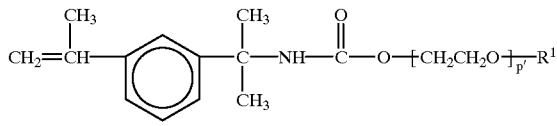

in which p ranges from 6 to 150 and $R^1$ is a $C_{18}$–$C_{26}$ alkyl radical, preferably $C_{20}$–$C_{24}$ linear, of plant origin, such as the docosyl radical.

The acrylic terpolymer is present in the cosmetic compositions of the invention in concentrations ranging from 0.01 to 20% by weight relative to the total weight of the composition, and preferably from 0.1 to 10% by weight.

According to the present invention, it is possible to use any polysaccharide or any polysaccharide derivative which is known per se, whether this is a homopolysaccharide or a heteropolysaccharide, of animal, plant, microbial, bacterial or synthetic origin.

In general, the polysaccharides and the derivatives thereof which can be used in the context of the present invention are those which are described in particular in "Encyclopedia of Chemical Technology, Kirk-Othmer, Third Edition, 1982, Volume 3, pp. 896–900, and Volume 15, pp. 439–458", in "Polymers in Nature, by E. A. MacGregor and C. T. Greenwood, published by John Wiley & Sons, Chapter 6, pp. 240–328, 1980" and in Industrial Gums—Polysaccharides and their Derivatives, edited by Roy L. Whistler, Second Edition, published by Academic Press Inc.", the content of these three publications being included in their entirety in the present application by way of reference.

According to the present invention, it is, of course, possible either to use one and the same polysaccharide and/or one of its derivatives, or, on the contrary, to use several polysaccharides and/or derivatives of different polysaccharides.

As examples of polysaccharides or of polysaccharide derivatives which are suitable for carrying out the invention, mention may be made in particular of glucans, modified or non-modified starches (such as those extracted, for example, from cereals such as wheat, corn, rice, vegetables such as haricot beans, tubers such as potatoes or cassava), amylose, amylopectin, glycogen, dextrans, β-glucans, celluloses and their derivatives (methylcelluloses, hydroxyalkylcelluloses, ethylhydroxyethylcelluloses, carboxymethylcelluloses), fructosans, inulin, levane, mannans, xylans, lignins, arabans, galactans, galacturonans, chitin, glucuronoxylanes, arabinoxylanes, xyloglucans, galactomannans, glucomannans, pectic acids and pectins, alginic acid and alginates, arabinogalactans, carrageenans, agars, glycosaminoglucans, gum arabics, gum tragacanths, ghatti gums, karaya gums, carob gums, guar gums and xanthan gums.

The preferred polysaccharides which can be used according to the invention are guar gums.

According to the invention, chemically modified or non-modified nonionic guar gums can be used.

The non-modified nonionic guar gums are, for example, the products sold under the name Vidogum GH 175 by the company Unipectine and under the name Jaguar C by the company Meyhall.

The modified nonionic guar gums which can be used according to the invention are preferably modified with $C_1$–$C_6$ hydroxyalkyl groups.

Among the hydroxyalkyl groups, mention may be made, for example, of hydroxymethyl, hydroxyethyl, hydroxypropyl and hydroxybutyl groups.

These guar gums are well known in the state of the art and can be prepared, for example, by reacting corresponding alkene oxides, such as, for example, propylene oxides, with guar gum so as to obtain a guar gum modified with hydroxypropyl groups.

The degree of hydroxyalkylation, which corresponds to the number of alkylene oxide molecules consumed by the number of free hydroxy functions present on the guar gum, preferably ranges from 0.4 to 1.2.

Such nonionic guar gums optionally modified with hydroxyalkyl groups are sold, for example, under the tradenames Jaguar HP8, Jaguar HP60 and Jaguar HP120, Jaguar DC293 and Jaguar HP105 by the company Meyhall, or under the name Galactasol 4H4FD2 by the company Aqualon.

The polysaccharides are used in the compositions of the invention in proportions of between 0.01 and 20% by weight and preferably between 0.1 and 10% by weight relative to the total weight of the composition.

The compositions according to the invention contain a cosmetically acceptable aqueous medium. They have a pH which can range from 3.5 to 11, preferably between 5.5 and 11 and even more preferably between 5.5 and 8.5.

The cosmetically acceptable medium for the compositions according to the invention consists more particularly of water and optionally of cosmetically acceptable organic solvents.

The organic solvents can represent from 0.5 to 90% of the total weight of the composition. They can be chosen from the group consisting of hydrophilic organic solvents, lipophilic organic solvents, amphiphilic solvents or mixtures thereof.

Among the hydrophilic organic solvents, mention may be made, for example, of linear or branched lower monoalcohols having from 1 to 8 carbon atoms, polyethylene glycols having from 6 to 80 ethylene oxide units, and polyols.

As amphiphilic organic solvents, mention may be made of polypropylene glycol (PPG) derivatives, such as esters of polypropylene glycol and of fatty acid, derivatives of PPG and of fatty alcohol, such as PPG-23 oleyl ether, and PPG-36 oleate.

As lipophilic organic solvents, mention may be made, for example, of fatty esters such as diisopropyl adipate, dioctyl adipate, alkyl benzoates and dioctyl malate.

In order for the cosmetic compositions of the invention to be more pleasant to use (softer when applied, more nourishing and more emollient), it is possible to add a fatty phase to the medium of these compositions.

The fatty phase can represent up to 50% of the total weight of the composition.

This fatty phase can contain an oil or a wax or mixtures thereof, and can also comprise fatty acids, fatty alcohols and fatty acid esters. The oils can be chosen from animal, plant, mineral or synthetic oils and in particular from liquid petroleum jelly, liquid paraffin, isoparaffins, poly-α-olefins, fluoro oils and perfluoro oils. Similarly, the waxes can be chosen from animal, fossil, plant, mineral or synthetic waxes which are known per se.

The compositions of the invention can contain adjuvants that are common in the cosmetics field, such as other standard gelling agents and/or thickeners; emulsifiers; surfactants; moisturizers; emollients; sunscreens; hydrophilic or lipophilic active agents such as ceramides; anti-free-radical agents; sequestering agents; antioxidants; preserving agents; acidifying or basifying agents; fragrances; fillers; dyestuffs; modified or non-modified, volatile or non-volatile silicones; reducing agents. The amounts of these various adjuvants are those used conventionally in the fields considered.

Needless to say, a specialist will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in any form which is suitable for topical application, in particular in the form of lotion-type solutions, in the form of aqueous or aqueous-alcoholic gels, in the form of vesicle dispersions or in the form of simple or complex emulsions (O/W, W/O, O/W/O or W/O/W emulsions) and can be of liquid,- semi-liquid or solid consistency, such as milks, creams, gels, cream-gels, pastes and sticks, and can optionally be packaged as an aerosol and can be in the form of mousses or sprays. These compositions are prepared according to the usual methods.

The compositions according to the invention can be used as rinse-out or leave-in hair products, in particular to wash, dye, care for, condition or straighten the hair, to maintain the hairstyle or to permanently or temporarily reshape the hair.

The compositions can be styling products such as hair-setting lotions, blow-drying lotions, fixing compositions and styling compositions. The lotions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray or a mousse for fixing or treating the hair.

The compositions of the invention can also be shampoos, rinse-out compositions or leave-in compositions, to be applied before or after shampooing, dyeing, bleaching, permanent-waving or straightening the hair.

The compositions of the invention can also be used as hygiene or care products, such as protective, treatment or care creams for the face, for the hands or for the body, protective or care body milks, and skincare or skin cleansing lotions, gels or mousses.

The compositions of the invention can also be used as antisun compositions.

The compositions can also consist of solid preparations constituting cleansing soaps or bars.

The compositions of the invention can also be used as oral care products such as toothpastes and mouthwashes.

The compositions can be make-up products such as face creams, foundations, mascaras, eyeliners, lipsticks or nail varnishes.

Another subject of the invention is a cosmetic, non-therapeutic treatment process for the skin, the scalp, the hair, the eyelashes, the eyebrows, the nails or mucous membranes, characterized in that a composition as defined above is applied to the keratinous support, according to the usual technique for using this composition, for example application of creams, gels, sera, lotions or milks to the skin, the scalp or mucous membranes.

The examples which follow illustrate the invention without being limiting in nature.

EXAMPLE 1

Leave-in styling gel

| | |
|---|---|
| Ethoxylated (40 EO) methacrylic acid/methyl acrylate/behenyl dimethylmetaisopropenyl-benzylisocyanate terpolymer as an aqueous 25% dispersion | 0.5 g AM |
| Hydroxypropylguar gum sold under the trade name Jaguar HP105 by the company Meyhall | 0.5 g AM |
| 2-Amino-2-methyl-1-propanol (AMP), qs pH adjusted to 7.5 | |
| Fragrance, preserving agent, dye qs | |
| Demineralized water qs | 100 g |

A thick, non-pasty gel which spreads very well on the hair is obtained. This gel makes the hair feel soft, makes it easy to disentangle and has good fixing power.

If the above terpolymer is replaced by the same amount of "Acrysol 44" polyurethane from Rohm & Haas, a very fluid, cloudy product is obtained.

If the terpolymer is replaced by the crosslinked acrylic acid/$C_{10}$/$C_{30}$ alkyl acrylate copolymer "Pemulen TR1" sold by Goodrich, a slightly pasty gel, which does not spread as well and has mediocre fixing power is obtained.

EXAMPLE 2

High-protection antisun gel

| | |
|---|---|
| 4-tert-Butyl-4'-methoxydibenzoyl methane ("Parsol 1789" sold by the company Roche) | 2 g |
| Benzene-1,4-di(3-methylidene-10-camphor-sulphonic acid), as an aqueous 33% solution | 3 g |
| 2-Ethylhexyl 2-cyano-3,3-diphenylacrylate ("Uvinul N 539" sold by the company BASF) | 10 g |
| Ethoxylated (40 EO) methacrylic acid/ methyl acrylate/behenyl dimethylmeta-isopropenylbenzylisocyanate terpolymer, | 0.55 g AM |

-continued

| | |
|---|---|
| as an aqueous 25% dispersion Xanthan gum sold under the name "Rhodicare S" by the company Rhone Poulenc | 0.8 g |
| 2,2,4,4,6,6,8-Heptamethylnonane | 4 g |
| Glycerol | 6 g |
| Propylene glycol | 6 g |
| Ethylenediaminetetra(methylenephosphonic acid), pentasodium salt, as an aqueous 33% solution | 0.3 g |
| Triethanolamine | 0.92 g |
| Denatured 96° ethyl alcohol | 4.5 g |
| Sterilized demineralized water qs | 100 g |

A creamy gel which spreads well on the skin is obtained.

What is claimed is:

1. Cosmetic composition for the treatment of keratinous material, comprising, in a cosmetically acceptable aqueous medium, at least one polysaccharide and an acrylic terpolymer comprising:
   a) about 20 to 70% by weight, of a carboxylic acid containing α,β-monoethylenic unsaturation;
   b) about 20 to 80% by weight, of a non-surfactant monomer containing monoethylenic unsaturation, which is different from a); and
   c) about 0.5 to 60% by weight of a nonionic urethane monomer which is the product of reaction of a monohydric nonionic surfactant with a monoisocyanate containing monoethylenic unsaturation.

2. Composition according to claim 1, wherein the carboxylic acid containing α,β-monoethylenic unsaturation a) is acrylic acid, methacrylic acid, itaconic acid or maleic acid.

3. Composition according to claim 2, wherein the carboxylic acid containing α,β-monoethylenic unsaturation a) is methacrylic acid.

4. Composition according to claim 1, wherein the non-surfactant monomer containing monoethylenic unsaturation b) is $C_1$–$C_4$ alkyl acrylates or methacrylates, styrene, vinyltoluene, vinyl acetate, acrylonitrile or vinylidene chloride.

5. Composition according to claim 4, wherein the non-surfactant monomer containing monoethylenic unsaturation is methyl or ethyl acrylate.

6. Composition according to claim 1, wherein the monohydric nonionic surfactant used to obtain the nonionic urethane monomer c) has the formula:

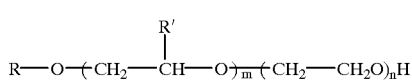

in which R is a $C_6$–$C_{30}$ alkyl or $C_8$–$C_{30}$ aralkyl group, R' is a $C_1$–$C_4$ alkyl group, n is an average number ranging about from 5 to 150 and m is an average number ranging about from 0 to 50, with the condition that n is at least as large as m and that n+m =5–150.

7. Composition according to claim 6, wherein R is a dodecyl, $C_{18}$–$C_{26}$ alkyl or ($C_8$–$C_{13}$) alkylphenyl group, m =0 and n is an average number ranging from about 5 to 150.

8. Composition according to claim 1 wherein the monoisocyanate containing monoethylenic unsaturation which is used to form the nonionic urethane monomer c) is α,α-dimethyl-m-isopropenyl benzyl isocyanate.

9. Composition according to claim 1 wherein the acrylic terpolymer is an aqueous dispersion obtained from methacrylic acid as component a), methyl acrylate as component b) and a nonionic urethane macromonomer of the following structure:

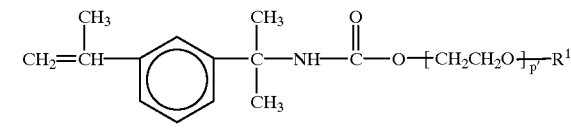

in which p ranges from 6 to 150 and $R^1$ is a $C_{18}$–$C_{26}$ alkyl radical.

10. Composition according to claim 1, wherein the acrylic terpolymer is present in concentrations ranging from 0.01 to 20% by weight, relative to the total weight of the composition.

11. Composition according to claim 1 wherein the polysaccharides are glucans, modified or non-modified starches amylose, amylopectin, glycogen, dextrans, β-glucans, celluloses or their derivatives fructosans, inulin, levane, mannans, xylans, lignins, arabans, galactans, galacturonans, chitin, glucuronoxylans, arabinoxylans, xyloglucans, galactomannans, glucomannans, pectic acids or pectins, alginic acid or alginates, arabino-galactans, carrageenans, agars, glycosaminoglucans, gum arabics, gum tragacanths, ghatti gums, karaya gums, carob gums, guar gums or xanthan gums.

12. Composition according to claim 11, wherein the polysaccharides are chemically modified or non-modified nonionic guar gums.

13. Composition according to claim 12, wherein the guar gums are modified with $C_1$–$C_6$ hydroxyalkyl groups.

14. Composition according to claim 13, wherein the guar gums are modified with a hydroxypropyl group.

15. Composition according claim 1, wherein the polysaccharides are present in concentrations ranging from 0.01 to 20% by weight, relative to the total weight of the composition.

16. Composition according to claim 1, wherein the composition has a pH ranging from 3.5 to 11.

17. Composition according to claim 1, wherein the cosmetically acceptable aqueous medium consists of water or of water and at least one organic solvent selected from the group consisting of hydrophilic, lipophilic and amphiphilic organic solvents and mixtures thereof.

18. Composition according to claim 1, further comprising at least one fatty substance, gelling agent and/or thickener, surfactant, moisturizer, emollient, sunscreen, hydrophilic or lipophilic active agent, anti-free-radical agent, sequestering agent, antioxidant, preserving agent, acidifying or basifying agent, fragrance, filler, dyestuff, silicone or reducing agent.

19. Composition according to claim 1, wherein the compositon it is in the form of an emulsion, a lotion, a gel, a vesicle dispersion, a paste or a solid stick or is packaged as an aerosol and is in the form of a mousse or a spray.

20. Composition according to claim 1, wherein the composition it is a rinse-out or leave-in hair product to wash, dye, care for, condition or straighten the hair, to maintain the hairstyle or to permanently or temporarily reshape the hair, or as an antisun composition.

21. Cosmetic, non-therapeutic treatment process for protecting keratinous material comprising applying an effective amount of composition as defined in claim 1 to the keratinous material.

22. Composition according to claim 1, wherein the acrylic terpolymer comprises about 25 to 55% by weight of the carboxylic acid containing α,β-monoethylenic unsaturation, about 30 to 65% by weight of the non-surfactant monomer containing monoethylenic unsaturation and about 10 to 50% by weight of the nonionic urethane monomer.

23. Composition according to claim 9, wherein R' is a linear $C_{20}$–$C_{24}$ alkyl radical of plant origin.

24. Composition according to claim 23, wherein the alkyl radical of plant origin is the docosyl radical.

25. Composition according to claim 10, wherein the acrylic terpolymer is in concentrations ranging from 0.1 to 10% by weight.

26. Composition according to claim 11, wherein the modified or non-modified starches are those extracted from cereals, vegetables or tubers.

27. Composition according to claim 11, wherein the celluloses or their derivatives are methylcelluloses, hydroxyalkylcelluloses, ethylhydroxyethylcelluloses or carboxymethylcelluloses.

28. Composition according to claim 15, wherein the polysaccharides are present in concentrations ranging from 0.1 to 10% weight.

29. Composition according to claim 16, wherein the pH range is from 5.5 to 8.5.

30. Process according to claim 21, wherein the keratinous material is skin, scalp, hair, eyelashes, eyebrows, nails or mucous membranes.

* * * * *